US010052466B2

(12) United States Patent
Chen et al.

(10) Patent No.: US 10,052,466 B2
(45) Date of Patent: Aug. 21, 2018

(54) TRANSDERMAL DRUG DELIVERING DEVICE

(71) Applicant: BEIJING SINOHANFANG PHARMACEUTICAL SCI. & TECH. CO., LTD., Beijing (CN)

(72) Inventors: Gang Chen, Beijing (CN); Meilin Wang, Beijing (CN)

(73) Assignee: Beijing Sinohanfang Pharmaceutical Sci. & Tech Co., Ltd., Beijing (CN)

( * ) Notice: Subject to any disclaimer, the term of this patent is extended or adjusted under 35 U.S.C. 154(b) by 435 days.

(21) Appl. No.: 14/655,641

(22) PCT Filed: Dec. 17, 2013

(86) PCT No.: PCT/CN2013/089618
§ 371 (c)(1),
(2) Date: Jun. 25, 2015

(87) PCT Pub. No.: WO2014/146464
PCT Pub. Date: Sep. 25, 2014

(65) Prior Publication Data
US 2015/0360013 A1   Dec. 17, 2015

(30) Foreign Application Priority Data
Mar. 22, 2013   (CN) .......................... 2013 1 0095217

(51) Int. Cl.
*A61F 13/00*   (2006.01)
*A61M 35/00*   (2006.01)
(Continued)

(52) U.S. Cl.
CPC .......... *A61M 35/00* (2013.01); *A61M 1/0088* (2013.01); *A61M 5/14248* (2013.01);
(Continued)

(58) Field of Classification Search
CPC .... A61M 35/00; A61M 1/0088; A61M 37/00; A61M 25/02; A61M 5/14248; A61M 2025/024
See application file for complete search history.

(56) References Cited

U.S. PATENT DOCUMENTS 4,921,199 A * 5/1990 Villaveces ............ A61M 25/02
                                                        248/314
5,538,736 A * 7/1996 Hoffmann .............. A61K 9/703
                                                        424/448
(Continued)

FOREIGN PATENT DOCUMENTS

CN         2242701 Y      12/1996
CN         1303717 A       7/2001
(Continued)

OTHER PUBLICATIONS

English translation of Description of Chen (CN 201061675).*
(Continued)

*Primary Examiner* — Tatyana Zalukaeva
*Assistant Examiner* — Ariana Zimbouski
(74) *Attorney, Agent, or Firm* — Ladas & Parry LLP (57) ABSTRACT

The present invention provides a transdermal drug delivering device which solves the problems that in the prior art, because absorptive force of an outer annular cavity caused by negative pressure is weakened, an application disk is prone to falling off. The transdermal drug delivering device comprises a first top, an annular outer wall, an annular inner wall, a first connecting tube and a middle annular cavity, wherein the annular outer and the annular inner wall are arranged on the two sides of the first top and fixedly with one side face of the first top, the first top, the annular outer wall and the annular inner wall constitute a first annular cavity, one end of the first connecting tube is communicated with the first annular cavity, the other end of the first connecting tube is communicated with negative pressure source, the central annular cavity is used for placing drug and comprises a first annular wall and a second top face, the first annular wall is connected with one end of annular inner wall through an annular bottom face, and the annular inner wall, the annular bottom face and the first annular wall form an
(Continued)

annular groove with the opening in the direction of the first top. The transdermal drug delivering device adapts to changing of curvature through the opening and the closing of the upper end of the annular groove, and therefore the first annular cavity is prevented from being controlled by the second top face, and the application disk applied on the portion out of flatness is not prone to falling off.

13 Claims, 4 Drawing Sheets

(51) Int. Cl.
- *A61M 37/00* (2006.01)
- *A61M 1/00* (2006.01)
- *A61M 25/02* (2006.01)
- *A61M 5/142* (2006.01)
- *A61M 5/158* (2006.01)

(52) U.S. Cl.
CPC ............ *A61M 25/02* (2013.01); *A61M 37/00* (2013.01); *A61M 1/0084* (2013.01); *A61M 2005/1586* (2013.01); *A61M 2037/0007* (2013.01)

(56) References Cited

U.S. PATENT DOCUMENTS

| | | | |
|---|---|---|---|
| 8,915,894 B1* | 12/2014 | Lonky | A61M 37/00 604/289 |
| 2011/0178456 A1 | 7/2011 | Aguilar-Mendoza et al. | |
| 2012/0022474 A1 | 1/2012 | Adoni et al. | |

FOREIGN PATENT DOCUMENTS

| | | |
|---|---|---|
| CN | 201061675 Y | 5/2008 |
| CN | 101284157 A | 10/2008 |
| CN | 202589932 U | 12/2012 |
| CN | 203169820 U | 9/2013 |
| WO | WO 2002/05890 A2 | 1/2002 |

OTHER PUBLICATIONS

English Abstract of CN203169820 U.
English Abstract of CN101284157 A.
English Abstract of CN201061675 Y.
English Abstract of CN2242701 Y.
English Abstract of CN1303717 A.
English Abstract of CN202589932 U.

* cited by examiner

TRANSDERMAL DRUG DELIVERING DEVICE

RELATED APPLICATION

This application is a national phase entry under 35 USC 371 of International Patent Application No PCT/CN2013/089618 filed on 17 Dec. 2013, which claims priority from China Patent Application No. 201310095217.0 filed on 22 Mar. 2013, the disclosures of which are incorporated in their entirety by reference herein.

TECHNICAL FIELD

The present invention relates to a medical device, in particular to a transdermal drug delivering device.

BACKGROUND ART

Chinese patent CN1303717 (application no. CN99126047.3), published on Jul. 18, 2001 described a transdermal drug delivering device. The application disk is applied on the skin and press the drug into the skin to treat. When the device is used to treat, the application disk is applied on the skin, and the outer annular cavity raise up the skin by absorptive force caused by the negative pressure because the outer annular cavity is communicated with the negative pressure source, and then the application disk is applied on the skin, at the same time, the central cavity is sealed completely, volatile constituent of the drug placed in the central cavity cannot escape out. In actual use, the application disk is prone to falling off in some situation:

1. The top of the outer annular cavity and the top of the central cavity is one flat or curve surface which connected closely. Because the application disk has a certain thickness and the top thereof is a distance from the skin, the application disk can be applied firmly on the portion flat of the body. However, when the application disk is applied on a portion out of flatness, such as nape, leg and arm which portion curvature is bigger, the top of the central cavity of the application disk will apply a great force to the top of the outer cavity, so that the absorptive force of the outer annular cavity caused by negative pressure is weakened, and the application disk is prone to falling off, and the treatment is affected.

2. the temperature in the central cavity is increased gradually due to being heated by the skin and/or outer heat source, and the volatilization of the drug is released gradually, so that the pressure of the central cavity is increased gradually and accelerate the transdermal delivering of the drugs. The increased pressure apply a outward raising force to the top of the central cavity. When the pressure is relative great, the top will extrude and produce a great force to the top of the outer cavity. The absorptive force of the outer annular cavity caused by negative pressure is weakened, and the application disk is prone to falling off, and the treatment is affected.

3. The vacuum tube is arranged on the top of the outer annular cavity in this solution. During the treatment, when the vacuum is stretched, for example being touched accidentally, the stretch force applied on the vacuum tupe will be delivered to the annular outer wall through the top of the annular outer cavity, therefore, the absorptive force caused by negative pressure is weakened and the application disk is prone to falling off and the treatment is affected.

Technical Problem

The present invention provides a transdermal drug delivering device to solve the problem of the prior art that the application disk is prone to falling off because the absorptive force of an outer annular cavity caused by the negative pressure is weakened.

Technical Solution

The technical solution is implemented as below:

A transdermal drug delivering device of the present invention comprises:

A first top, an annular outer wall and an annular inner wall, wherein the outer wall and the inner wall are arranged on the two sides of the first top and fixedly connected with one side of the first top, and constitute a first annular cavity together with the first top;

a first connecting tube, wherein one end of the first connecting tube is communicated with the first annular cavity, and the other end is communicated with a negative pressure source;

a central annular cavity 6 for placing drug;

The central annular cavity comprises a first annular wall and a second top, and the first annular wall is connected with one end of the annular inner wall through the first annular bottom;

The annular inner wall, the first annular bottom and the first annular wall form a first annular groove opening towards the direction of the first top.

Preferably, the transdermal drug delivering device includes a second annular wall, a third annular wall and a second annular bottom, and these three components constitute a second annular groove opening towards to the second top.

Preferably, the transdermal drug delivering device includes a fourth annular wall and a second connecting tube. The fourth annular wall and the second connecting tube constitute a second annular cavity. The first annular wall, the fourth annular wall and the second top constitute a central annular separation cavity. One end of the second connecting tube is communicated with the second annular cavity, and the other end is communicated with the negative pressure source.

Preferably, the transdermal drug delivering device further includes a connecting column for supporting the first connecting tube, which is arranged on the second top. One end of the first connecting tube is communicated with the first annular cavity by passing through the connecting column, and the other end is communicated with a negative pressure source.

Preferably, the first connecting tube further includes a negative pressure source connecting section and a first annular cavity connecting section, wherein the negative pressure source connecting section is communicated with the first annular cavity connecting section, and one end of the first annular cavity connecting section is communicated with the first annular cavity, and the other end is communicated with the second annular cavity where the first annular cavity connecting section is connected with the negative pressure source connecting section.

Preferably, the length of the first annular cavity connecting section is great than the linear distance on horizontality between the first annular cavity and the second annular cavity.

Preferably, the transdermal drug delivering device further includes a third annular wall and a fourth annular wall. The third annular wall and the second top constitute a third annular cavity. The fourth annular wall and the second top constitute a fourth annular cavity. The second annular cavity, the third annular cavity and the fourth annular cavity are arranged on the second top with equal distance between each other.

Preferably, the first connecting tube includes a second annular cavity connecting section and a third annular cavity connecting section, wherein, one end of the second annular cavity connecting section is communicated with the third annular cavity, and the other end is communicated with a negative pressure source. One end of the third annular cavity connecting section is communicated with the fourth annular cavity, and the other end is communicated with a negative pressure source.

Preferably, the device further includes an annular cushion preventing the skin from being stretched excessively by the negative pressure and being damaged. The annular cushion is arranged in the first annular cavity.

Preferably, the annular cushion is a ventilative annular cushion.

Advantageous Effect of the Present Invention

Advantageous Effect

The annular inner wall, the first annular bottom and the first annular wall constitute the first annular groove. When the device is applied on the portion out of flatness such as nape, leg or arm, because the first annular groove separate the first top from the second top, the first annular groove adapts to changing of curvature through the opening and the closing of the top thereof, and therefore avoid the first annular cavity controlled by the second top, and the device applied on the portion out of flatness is not prone to falling off.

Furthermore, through arranging the second annular cavity which can be applied on the skin by connecting the second connecting tube with the negative pressure source, so that the top outward extrude and deformation degree caused by the air pressure can be reduced, and then the device is not prone to falling off.

Furthermore, because the first connecting tube is fixed on the top of the central cavity through the connecting column, the force is firstly applied on the second top, when the first connecting tube is stretched, and the second top can defuse the force by accordingly elastic deformation, so that prevent the force from being delivered to the first annular cavity directly, and prevent the absorptive force of the first annular cavity from being weakened, thus, the device is not prone to falling off. When the negative pressure source connecting section is connected with the first annular cavity connecting section, the absorptive force of the first cavity from being weakened, since the force applied on the first connecting tube is delivered to the second top, thus, the device is not prone to falling off.

DESCRIPTION OF FIGURES

In order to explain the technical solution of the present invention or the prior art more clearly, there will be a simple introduction of the figures used for the explaining of the embodiment or the prior art. It is obviously that the figures described below are only embodiments of the present invention. For the skilled person in the art, other figures can be achieved according to these figures without creative labor.

In the figure:
1. first top; 2. annular outer wall; 3. annular inner wall; 4. first annular cavity; 5. first connecting tube; 6. central annular cavity; 7. first annular wall; 8. second top; 9. first annular bottom; 10. annular groove; 11. fourth annular wall; 12. second connecting tube; 13. second annular cavity; 14. central annular separation cavity; 15. connecting column; 16. negative pressure source connecting section; 17. first annular cavity connecting section; 18. third annular cavity; 19. fourth annular cavity; 20. skin; 21. second annular wall; 22. third annular wall; 23. second annular bottom; 24. second annular groove; 25. annular cushion; 26. an annular passage.

EMBODIMENTS OF CARRYING OUT THE INVENTION

The technical solution of the embodiments of the present invention will be described clearly and completely combining the figures. It is obviously that the embodiments described are only one part of the application not the whole. Based on the embodiments of the present invention, all other embodiments achieved by the person skilled in the art without creative labor are all included in the scope of present invention.

According to FIG. 1-7, the transdermal drug delivering device of the present invention comprises:

A first top 1, an annular outer wall 2 and an annular inner wall 3, and the latter are arranged on the two sides of the first top 1 and fixedly connected with one side of the first top 1, and constitute a first annular cavity 4 together with the first top 1;

a first connecting tube 5, wherein one end of the first connecting tube 5 is communicated with the first annular cavity 4, and the other end is communicated with a negative pressure source.

a central annular cavity 6 for placing drug, the central annular cavity 6 comprises a first annular wall 7 and a second top 8, and the first annular wall 7 is connected with one end of the annular inner wall 3 through an annular bottom 9;

the annular inner wall 3, the annular bottom 9 and the first annular wall 7 form a first annular groove 10 opening towards the direction of the first top 1.

Because the first annular groove 10 separates the first top 1 from the second top 8, When the device is applied on the portion out of flatness such as nape, leg or arm, the first annular groove 10 adapts to changing of curvature through the opening and the closing of the top thereof, and therefore avoid the first annular cavity 4 controlled by the second top 8, and the device applied on the portion out of flatness is not prone to falling off. Wherein the first annular groove 10 is formed by the annular inner wall 3 and the first annular bottom 9 and the first annular wall 7

Figure 1:
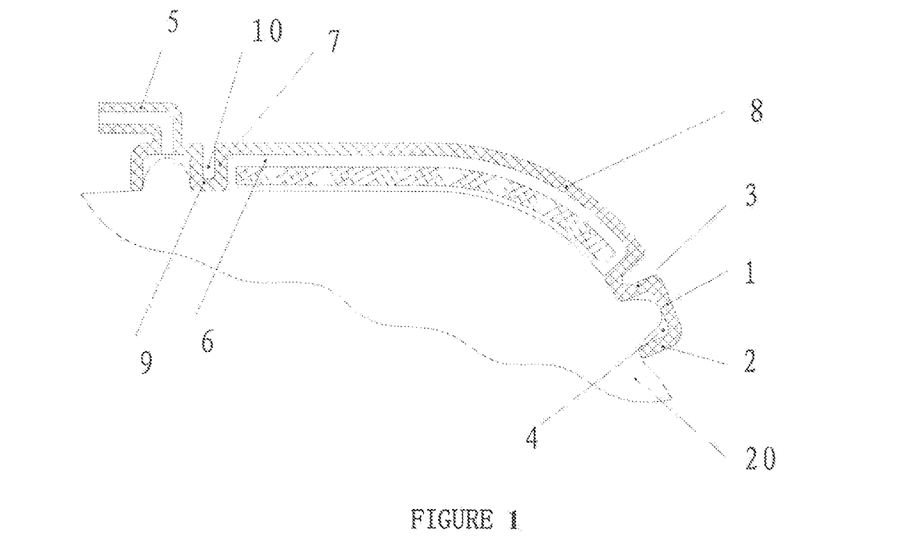
FIG. 1 shows a first embodiment of a transdermal drug delivering device according to the present invention.

In one embodiment of the present invention, the first top 1, the annular outer wall 2 and the annular inner wall 3 constitute the first annular cavity 4, wherein one end of the first connecting tube 5 is communicated with the first annular cavity 4, the other end of the first connecting tube 5 is communicated with the negative pressure source. The first annular wall 7 and the second top 8 constitute the central annular cavity 6, wherein the first annular wall 7 is connected with one end of the first annular bottom 9, and the other end of the first annular bottom 9 is connected with the annular inner wall 3, therefore, the annular inner wall 3, the first annular bottom 9 and the first annular wall 7 constitute the first annular groove 10. In the use phase, the first annular cavity 4 and the central annular cavity 6 are applied on the skin 20, and the drugs are placed in the central annular cavity 6. Then, the skin 20 is raised by the absorptive force caused by the negative pressure source through the first connecting tube 5, so that the first annular cavity 4 can be adsorbed on the skin 20, at the same time, the central annular cavity 6 can be completely sealed, therefore, the drugs placed in the cavity 6 can not escape out after volatilization. Furthermore, when the device is applied on the portion out of flatness, the open end of the first annular groove 10 is opening to adapt to the changing of the curvature, and the second top 8 is prevented from being controlled by the first top, and the absorptive force of the first annular cavity 4 is prevented from being weakened, so the device is not prone to falling off.

Figure 5:
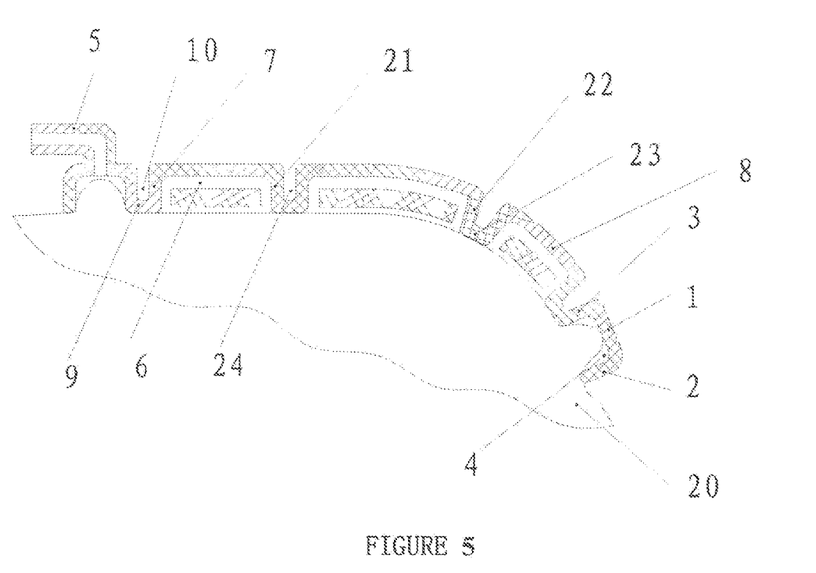
FIG. 5 shows a fifth embodiment of a transdermal drug delivering device according to the present invention.

As shown in the FIG. 5, in another embodiment of the present invention, the transdermal drug delivering device preferably includes a second annular wall 21, a third annular wall 22 and a second annular bottom 23, and these three components constitute a second annular groove 24 opening towards to the second top 8.

One end of the second annular bottom 23 is connected with the second annular wall 21, and the other end of the second annular bottom 23 is connected with the third annular wall 22. The second annular wall 21, the second annular bottom 23 and the third annular wall 22 constitute a second annular groove 24. When the device is applied on a portion with great curvature, the second annular groove 24 coordinates the first annular groove 10, both grooves open ends are opening to adapt to the curvature of the portion with great curvature. With this design, the absorptive force of the first annular cavity 4 can be further prevented from being weakened, and the device is not prone to falling off.

Figure 2:
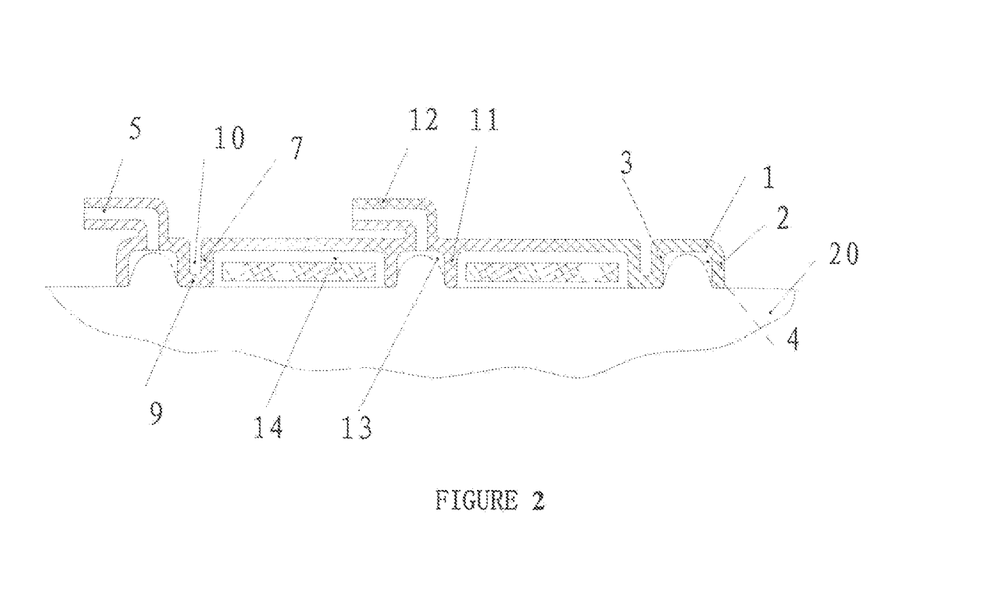
FIG. 2 shows a second embodiment of a transdermal drug delivering device according to the present invention.

As shown in the FIG. 2, in another embodiment of the present invention, the transdermal drug delivering device preferably includes a fourth annular cavity 11 and a second connecting tube 12. The fourth annular cavity 11 and the second top 8 constitute a second annular cavity 13. The first annular wall 7, the fourth annular wall 11 and the second top 8 constitute a central annular separation cavity 14. One end of the second connecting tube 12 is communicated with the second annular cavity 13, and the other end is communicated with a negative pressure source.

The fourth annular wall 11 and the second top 8 constitute the second annular cavity 13 which is connected with the negative pressure source by the second connecting tube 12. The central annular cavity 6 is separated to central annular separation cavities 14 by the second annular cavity 13. In this case, the second connecting tube 12 is directly connected with the negative pressure source. Of course, the second connecting tube 12 can also be connected with the first connecting tube 5, then be connected with the negative pressure source through the first connecting tube 5. The cost can be saved in a certain degree in this manner. It is depended on the actual requirements, and there will be no limitation. In the use phase, the skin 20 which is under the second annular cavity 13 is absorbed by the second connecting tube 12 through the negative pressure source, that is to say, the central part of the second top 8 is anchored, and it will not expand and project out in the situation when the air expand or the pressure is increased gradually, so that the absorptive force of the first annular cavity 4 can be prevented from being weakened, and the device is not prone to falling off.

Figure 3:
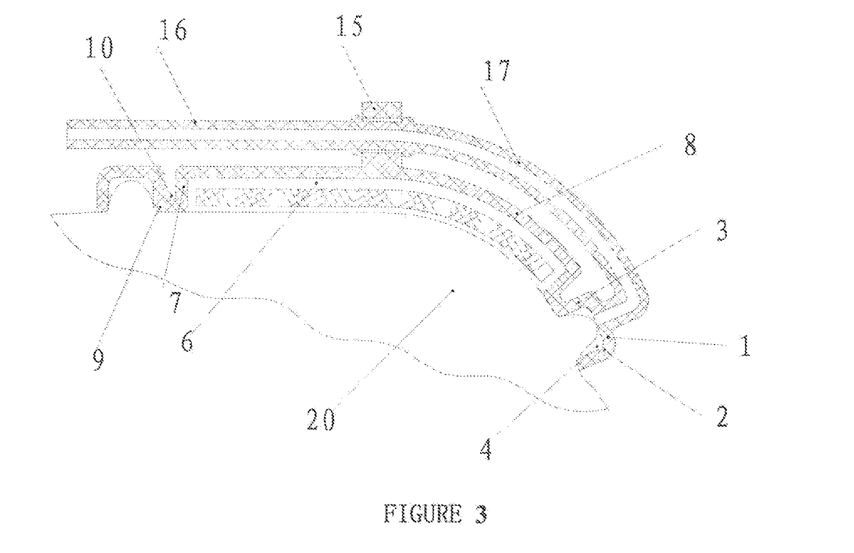
FIG. 3 shows a third embodiment of a transdermal drug delivering device according to the present invention.

As shown in the FIG. 3, in another embodiment of the present invention, the transdermal drug delivering device preferably includes a connecting column 15 for supporting the first connecting tube 5. The connecting tube 5 is arranged on the second top 8. One end of the first connecting tube 5 is connected with the first annular cavity 4 by passing through the connecting column 15, and the other end is communicated with the negative pressure source.

In this embodiment, a connecting column 15 is provided on the second top 8, one end of the first tube 5 pass through the connecting column 15 and fixed on the connecting column 15, the first connecting tube 5 is communicated with the first annular cavity 4 by passing through one end of the connecting column 15; length of the first tube 5 passed through the end of the connecting column 15 is bigger than linear distance between central point of the first top 1 on horizontality and central point of the first annular cavity 4. That is to say, when the second top 8 is on horizontality, the first tube 5 is curve. Length of the first tube 5 can adapt to the enlarged distance when adsorbed on body portion with large curvature, and won't restrain the first top; at the same time, because the first connecting tube 5 is fixed on the second top 8 through the connecting column 15, the force is firstly applied on the second top 8, when the first connecting tube 5 is stretched, and the second top 8 can defuse the force by accordingly elastic deformation, so that prevent the force from being delivered to the first annular cavity 4 directly, and prevent the absorptive force of the first annular cavity 4 from being weakened, thus, the device is not prone to falling off.

Figure 4:
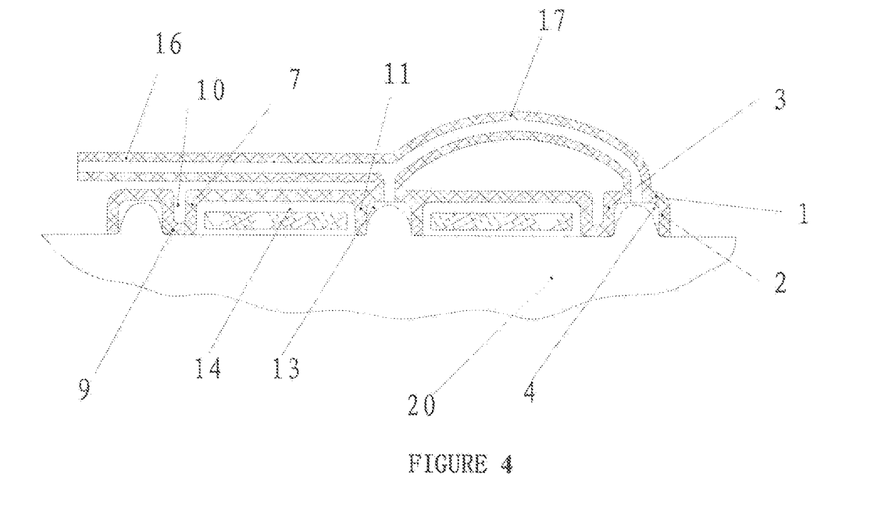
FIG. 4 shows a fourth embodiment of a transdermal drug delivering device according to the present invention.

Preferably, the first connecting tube 5 further includes a negative pressure source connecting section 16 and a first annular cavity connecting section 17. The negative pressure source connecting section 16 is communicated with the first annular cavity connecting section 17. One end of the first annular cavity connecting section 17 is communicated with the first annular cavity 4, and the other end is communicated with the second annular cavity 13 where the negative pressure source connecting section 16 is communicated with the first annular cavity connecting section 17.

Preferably, the length of the first annular cavity connecting section 17 is great than the linear distance on horizontality between the first annular cavity 4 and the second annular cavity 13.

As shown in the FIG. 4, in another embodiment of the present invention, the first connecting tube 5 includes a negative pressure source connecting section 16 and a first annular cavity connecting section 17. One end of the first annular cavity connecting section 17 is communicated with the first annular cavity 4, and the other end is communicated with the second annular cavity 13 at where the negative pressure source connecting section 16 is communicated with the first annular cavity connecting section 17. Wherein, the length of the first annular cavity 17 is great than the linear distance on horizontality between the first annular cavity 4 and the second annular cavity 13. When the device is applied on the portion with great curvature, the first annular cavity connecting section 17 has enough length to adapt to the increasing distance between two ends so that avoiding the first top controlled. At the same time, by the negative pressure source, the skin 20 which is under the second annular cavity 13 is absorbed through the first connecting tube 5. That is to say, the central part of the second top 8 is anchored, and it will not expand and project out in the situation when the air expand or the pressure is increased gradually, so that the absorptive force of the first annular cavity 4 can be prevented from being weakened, and the device is not prone to falling off.

Figure 7:
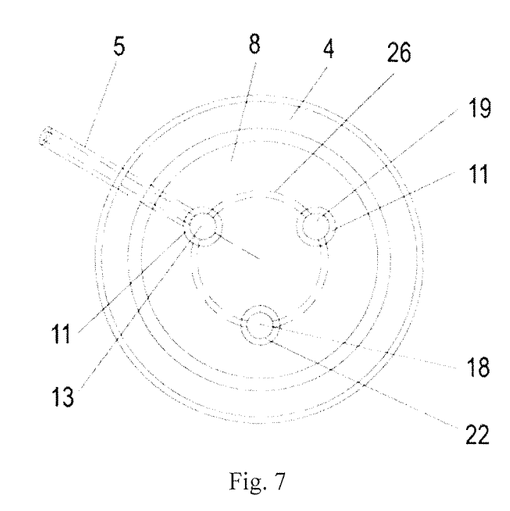
FIG. 7 shows an embodiment of a central annular cavity of a transdermal drug delivering device according to the present invention.

Preferably, the transdermal drug delivering device further includes a third annular wall 22 and a fourth annular wall 11. The third annular wall 22 and the second top 8 constitute a third annular cavity 18. The fourth annular wall 11 and the second top 8 constitute a fourth annular cavity 19. The second annular cavity 13, the third annular 18 and the fourth annular cavity 19 are arranged on the second top 8 with equal distance between each other.

As shown in the FIG. 7, in another embodiment of the present invention, The third annular wall 22 and the second top 8 constitute a third annular cavity 18. The fourth annular wall 11 and the second top 8 constitute a fourth annular cavity 19. The second annular cavity 13, the third annular 18 and the fourth annular cavity 19 are arranged on the second top 8 with equal distance between each other. There is preferably provided with three annular cavities, four, five or more annular cavities can all be considered to be provided to prevent the second top 8 from expanding and projecting towards out. In this embodiment, an annular passage 26 is provided in the second top 8 communicating the second annular cavity 13, the third annular cavity 18 and the fourth annular cavity 19. The second top 8 is anchored at three parts, so that the second top 8 can be restrained effectively and can not expand and project out. Thus, the absorptive force of the first annular cavity 4 can be prevented from being weakened and is not prone to falling off.

In another embodiment of the present invention, preferably, the first connecting tube 5 includes a second annular cavity connecting section and a third annular cavity connecting section, wherein, one end of the second annular cavity connecting section is communicated with the third annular cavity 18, and the other end is communicated with a negative pressure source. One end of the third annular cavity connecting section is communicated with the fourth annular cavity 19, and the other end is communicated with a negative pressure source.

In this embodiment, by the separate communication of the second annular cavity connecting section with the second annular cavity 13 and the third annular cavity connecting section with the fourth annular cavity 19, the second top 8 is anchored and restrained effectively at three parts thereof by the negative pressure before drug delivering, so that the second top 8 unable to expand and project outwardly, thus the absorptive force of the first annular cavity 4 can be prevented from being weakened, and the application disk is not prone to falling off.

Figure 6:
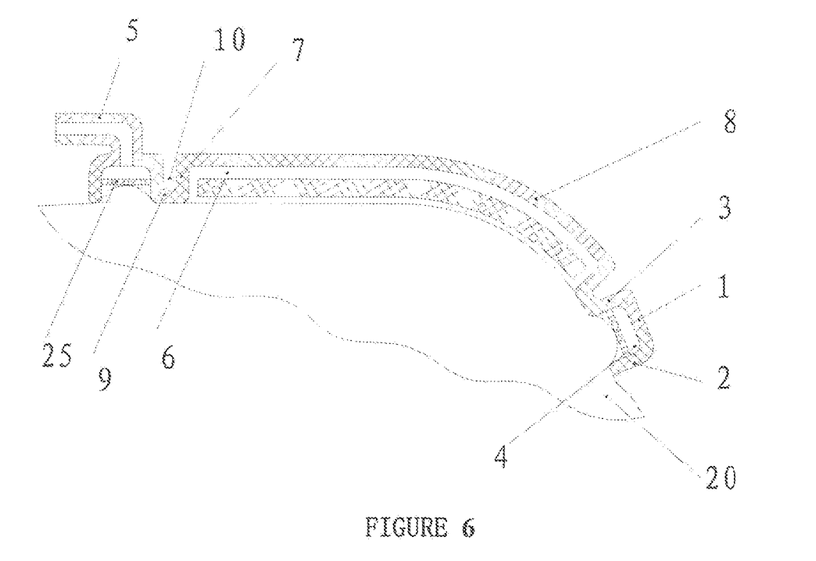
FIG. 6 shows a sixth embodiment of a transdermal drug delivering device according to the present invention.

As shown in the FIG. 6, in another embodiment of the present invention, preferably, the device further includes an annular cushion 25 preventing the skin from being stretched excessively by the negative pressure and being damaged. The annular cushion 25 is arranged in the first annular cavity 4.

Preferably, the annular cushion 25 is a ventilative annular cushion 25.

The annular cushion 25 is provided in the first annular cavity 4. The skin 20 is stretched by the negative pressure and against the annular cushion 25 when the skin 20 is stretched to a certain degree, so that the skin 20 is prevented from being stretched excessively and damaged. The annular cushion 25 can be provided in the second annular cavity 13 and connected to one or two sides of the first annular cavity 4. Alternatively, one side of the annular cushion 25 is connected to the first top 1, that is to say, the annular cushion 25 can be applied on the first top 1 by gooney. The annular cushion can also be fixed in the first annular cavity 4 in other manner, but there will be no description. The annular cushion 25 of this embodiment can be ventilative annular cushion, thus, the skin 20 can be raised effectively by the negative pressure source. Of course, the annular cushion 25 can also be cotton cushion, non-woven fabrics cushion or others which can ensure the ventilation and prevent the skin 20 from being stretched excessively and damaged.

The above described are only preferable embodiments of the present invention, it is not used to limit the invention, any modifications, equivalent replacements and improvements within the spirit and principle of the invention are all included in the scope of the present invention.

The invention claimed is:

1. A transdermal drug delivering device comprising:
    a first top (1),
    an annular outer wall (2) and an annular inner wall (3) arranged on two sides of the first top (1) and fixedly connected with one side of the first top (1), forming a first annular cavity (4) together with the first top (1),
    a first connecting tube (5), wherein one end of the first connecting tube (5) is communicated with the first annular cavity (4), and another end of the first connecting tube (5) is adapted to be coupled to a negative pressure source,
    a central annular cavity (6) for placing a drug,
    characterized in that:
    the central annular cavity (6) comprises a first annular wall (7) and a second top (8), and the first annular wall (7) is connected with one end of the annular inner wall (3) through an annular bottom (9),
    the annular inner wall (3), the annular bottom (9) and the first annular wall (7) form a first annular groove (10) opening towards the direction of the first top (1), and
    said device further includes a connecting column (15) for supporting the first connecting tube (5), said connecting column (15) being located on the second top (8).

2. A transdermal drug delivering device comprising:
    a first top (1),
    an annular outer wall (2) and an annular inner wall (3) arranged on two sides of the first top (1) and fixedly connected with one side of the first top (1), forming a first annular cavity (4) together with the first top (1),
    a first connecting tube (5) comprising a negative pressure source connecting section 16 and a first annular cavity connecting section (17), wherein the first annular cavity connecting section (17) is communicated with the first annular cavity (4), and another end of the first connecting tube (5) is adapted to be coupled to a negative pressure source,
    a cavity (14) for placing a drug,
    characterized in that
    the cavity for placing a drug (14) comprises a first annular wall (7) and a second top (8), and the first annular wall (7) is connected with one end of the annular inner wall (3) through an annular bottom (9),
    the annular inner wall (3), the annular bottom (9) and the first annular wall (7) form a first annular groove (10) opening towards the direction of the first top (1), a fourth annular wall (11), and a second connecting tube (12), wherein the fourth annular wall (11) and the second top (8) form a second annular cavity (13), wherein one end of the negative pressure source connecting section (16) is communicated with the first annular cavity connecting section (17) and another end of the negative pressure source connecting section (16) is adapted to be coupled to the negative pressure source, and wherein one end of the first annular cavity connecting section (17) is communicated with the first annular cavity (4) and another end of the first annular cavity connecting section (17) is communicated with the second annular cavity (13) at where the first annular cavity connecting section (17) is connected with the negative pressure source connecting section (16).

3. The transdermal drug delivering device according to claim 2, characterized in that a length of the first annular cavity connecting section (17) is greater than a linear distance between the first annular cavity (4) and the second annular cavity (13).

4. The transdermal drug delivering device according to claim 3, characterized in that the device further comprises a third annular cavity (18) and a fourth annular cavity (19) wherein said second, third and fourth annular cavities are arranged on the second top (8) with equal distance between each other.

5. The transdermal drug delivering device according to claim 4, characterized in that the first connecting tube (5) comprise:
a second annular cavity connecting section, wherein one end of the second annular cavity connecting section is communicated with the third annular cavity (18), another end of the second annular cavity connecting section is adapted to be coupled to the negative pressure source,
a third annular cavity connecting section, wherein one end of the third annular cavity connecting section is communicated with the fourth annular cavity (19), another end of the third annular cavity connecting section is adapted to be coupled the negative pressure source.

6. The transdermal drug delivering device according to claim 1, characterized in that the device further comprises an annular cushion (25) preventing the skin from being stretched by the negative pressure beyond the annular cushion and being damaged, and that the annular cushion (25) is arranged in the first annular cavity (4).

7. The transdermal drug delivering device according to claim 6, characterized in that the annular cushion (25) is a ventilative annular cushion (25).

8. The transdermal drug delivering device according to claim 2, characterized in that the device further comprises an annular cushion (25) preventing the skin from being stretched by the negative pressure beyond the annular cushion and being damaged, and that the annular cushion (25) is arranged in the first annular cavity (4).

9. The transdermal drug delivering device according to claim 3, characterized in that the device further comprises an annular cushion (25) preventing the skin from being stretched by the negative pressure beyond the annular cushion and being damaged, and that the annular cushion (25) is arranged in the first annular cavity (4).

10. The transdermal drug delivering device according to claim 4, characterized in that the device further comprises an annular cushion (25) preventing the skin from being stretched by the negative pressure beyond the annular cushion and being damaged, and that the annular cushion (25) is arranged in the first annular cavity (4).

11. The transdermal drug delivering device according to claim 5, characterized in that the device further comprises an annular cushion (25) preventing the skin from being stretched by the negative pressure beyond the annular cushion and being damaged, and that the annular cushion (25) is arranged in the first annular cavity (4).

12. The transdermal drug delivering device according to claim 4, wherein the second top (8) comprises an annular passage, the annular passage communicating the second annular cavity (13), the third annular cavity (18) and the fourth annular cavity (19).

13. The transdermal drug delivering device according to claim 12, characterized in that the device further comprises an annular cushion (25) preventing the skin from being stretched by the negative pressure beyond the annular cushion and being damaged, and that the annular cushion (25) is arranged in the first annular cavity (4).

* * * * *